US006099840A

United States Patent [19]

Thomas et al.

[11] Patent Number: 6,099,840
[45] Date of Patent: Aug. 8, 2000

[54] HEPATITIS B VACCINE

[75] Inventors: Howard Christopher Thomas; William Frederick Carman, both of London, United Kingdom

[73] Assignee: Imperial College of Science, Technology and Medicine, London, United Kingdom

[21] Appl. No.: 08/479,609

[22] Filed: Jun. 7, 1995

Related U.S. Application Data

[62] Division of application No. 08/339,281, Nov. 7, 1994, which is a continuation of application No. 07/927,489, filed as application No. PCT/GB91/00444, Mar. 25, 1991.

[30] Foreign Application Priority Data

Apr. 29, 1990 [GB] United Kingdom .................. 9007024

[51] Int. Cl.[7] .......................... C07K 16/00; C12P 21/08; A61K 39/42

[52] U.S. Cl. .................................... 424/139.1; 424/159.1; 424/161.1; 424/189.1; 424/227.1; 530/387.9; 530/388.3; 530/389.4

[58] Field of Search ............................ 424/189.1, 227.1, 424/139.1, 159.1, 161.1; 530/388.3, 389.4, 387.9

[56] References Cited

PUBLICATIONS

Ashton–Rickardt et al., "Mutants of the Hepatitis B Virus Surface Antigen . . . ," J Med Virol. 29:196–203(1989).
Zanetti et al., "Hepatitis B Variant in Europe," The Lancet, Nov. 12, 1988 : 1132–33.

*Primary Examiner*—Michael P. Woodward
*Assistant Examiner*—Mary K Zeman
*Attorney, Agent, or Firm*—Nixon & Vanderhye

[57] ABSTRACT

A variant HBsAg protein of fragment thereof displaying the antigenicity of Hepatitis B virus surface antigen is disclosed, in which the variant protein or fragment thereof (vHBsAg) comprises a modified a determinant in which there is an amino acid other than glycine at position 145 of the HBsAg sequence. A vaccine comprising the vHBsAg is provided, as it is a kit for diagnostic in vitro detection of anti-vHBsAg antibodies and an antibody preparation comprising anti-vHBsAg antibodies.

10 Claims, 3 Drawing Sheets

HEPATITIS B VACCINE

This is a division of application Ser. No. 08/339,281 filed Nov. 7, 1994, which is a continuation of application Ser. No. 07/927,489 filed Nov. 16, 1992 (now abandoned), which is the U.S. counterpart of PCT/GB91/00444 filed Mar. 25, 1991 which claims priority from British application 9007024.4 filed Mar. 29, 1990.

This invention relates to recombinant DNA molecules that code for polypeptides with the specificity of a hepatitis B viral antigen.

More particularly this invention relates to a vaccine composition for stimulating the production of antibodies in humans to a variant hepatitis B virus.

Infection with hepatitis B virus (HBV) is a serious, widespread problem but vaccines which can be used for mass immunisation are now available, for example the product 'Engerix-B' (SmithKline Beecham p.l.c.) which is obtained by genetic engineering techniques.

The cloning of genomes of Hepatitis B virions of different serotypes is well known in the art; see Miller et al., *Hepatology,* 9 (1989) page 322 and references therein. Dane particles which are hepatitis B virions and which are isolatable from infected patients have a diameter of about 42 nm. Each consists of an envelope comprising the hepatitis B surface antigen (HBsAg), a capsid (HBcAg), an endogenous polymerase and a DNA genome. A third polypeptide, 'e' antigen (HBeAg) is made by hepatitis B virus and found in solubulized form in serum.

Commercially available vaccines against HBV comprise Hepatitis B virus surface antigen (HBsAg) either in native or recombinant form. The authentic Hepatitis B virus surface antigen can be recovered from plasma of infected individuals as a particle of about 22 nm comprised of two proteins known as P24 and its glycolsylated derivative GP28, both of which are encoded by the 226 amino acid coding sequence on the HBV genome known as the S protein coding sequence or HBV S-gene; see Tiollais et al, *Nature,* 317 (1985), page 489 and references therein. The complete amino acid sequence of, and nucleotide sequence encoding, HBsAg is given in Valenzuela et al, *Nature,* 280 (1979), page 815. The numbering system used by Tiollais et al. (loc cit.) to define nucleotide and amino acid positions is used herein.

Insertion of HBV S-gene coding sequences under the control of yeast promoters on expression vectors to enable expression of HBsAg in *S. cerevisiae* for vaccine production has been described by, for example, Harford et al in *Develop. Biol. Standard.* 54: page 125 (1983), Valenzuela et el., *Nature* 298, page 347 (1982) and Bitter et al., *J. Med. Virol.* 25, page 123 (1988). Expression in *Pichia pastoris* has also been described by Gregg et al, *Biotechnology,* 5 (1987), page 479 (see also European Patent Application Publication No. 0 226 846) as has expression in *Hansenula polymorpha* (see EP-A- 0 299 108).

Vaccines may also be prepared from hybrid immunogenic particles comprising HBsAg protein as described in European Patent Application Publication No. 0 278 940.

Such particles can contain, for example, all or part of parts of the HBsAg precursor protein encoded by the coding sequence which immediately precedes the HBV-S gene on the HBV genome, referred to herein as the Pre S coding sequence. The Pre S coding sequence normally codes for 163 amino acids (in the case of the ay HBV sub type) and comprises a Pre S1 coding sequence and a Pre S2 coding sequence. The latter codes for 55 amino acids and immediately precedes the S protein coding sequence (see EP-A-0 278 940 for further details).

Antigenic subtypes of HBV are defined serologically and have been shown to be due to single base changes in the region of the genome encoding HBsAg (Okamoto et al., *J. Virol.,* 1987, 74, 5463–5467). However, all known antigenic subtypes contain the 'a' determinant consisting of amino acids 124 to 147 of HBsAg. Antibody to the 'a' determinant confers protection against all subtypes. It has been shown by in vitro mutagenesis that the cysteine at position 147 and the proline at position 142 are important for the exhibition of full antigenicity of the 'a' determinant (Ashton et al, *J. Med. Virol.,* 1989, 29, page 196).

During the last decade, several putative variants of hepatitis B virus (HBV) have been described.

McMahon et al have reported that substitution of arginine for glycine in the putative monoclonal antibody binding domain of HBsAg was found (as deduced by DNA sequence analysis) in a liver transplant patient treated with anti-HBsAg monoclonal antibody (Cold Spring Harbor Symposium on the Molecular Biology of Hepatitis B viruses, September, 1989). This result does not however provide any incentive to synthesise a variant HBsAg amino acid sequence or develop a vaccine composition based thereon.

In another report, children and adults were found with circulating hepatitis B surface antigen, indicating viral replication, despite the presence of specific antibody (anti-HBs) after immunisation with one of two licensed hepatitis B vaccines (Zanetti et al. *Lancet,* November 1988, page 1132). Analysis of the HBsAg with monoclonal antibodies revealed that the circulating antigen did not carry the 'a' determinant or that this determinant was masked. It was concluded that emergence of a variant of hepatitis B virus had been detected, possibly due to epidemiological pressure associated with immunisation in an endemic area of infection. The variant was, however, not characterised further.

From the work of Zanetti et al. it is clear that a potential disadvantage with presently available hepatitis B vaccines is that they may, at least in a host with a predisposing immunogenetic make-up, cause the appearance of an 'escape mutant', i.e. a replicating infectious virus that has mutated away from neutralising immunity. Such a variant virus clearly has the capacity to cause disease and may be assumed to be transmissible. The variant virus may therefore give rise to a serious immunisation problem since it is not effectively neutralised by antibodies produced by vaccines based on normal HBsAg.

The present invention overcomes, or at least mitigates, the above disadvantages associated with known HVB vaccines.

According to the present invention there is provided an HBsAg protein or a fragment thereof displaying the antigenicity of HBV surface antigen, characterised in that the protein or fragment thereof comprises a modified 'a' determinant in which there is an amino acid other than glycine at position 145 of the HBsAg sequence.

It is to be understood that the variant HBsAg may also include Pre S sequences if so desired.

The variant HBsAg protein or fragment thereof according to the invention is hereinafter abbreviated to vHBsAg.

It will be appreciated that the vHBsAg is not in a 'naturally occurring' form but is synthetic or highly purified material, free of blood products.

Preferably the vHBsAg of the invention corresponds to full length HBsAg and is identical to normal HBsAg except for the altered amino acid residue at position 145.

Preferably the vHBsAg is in highly purified form, for example in a state of purity greater than 75%, more preferably greater than 90%, and most preferably is 95–100% pure.

In a further aspect of the present invention there is provided a vaccine composition comprising an immunoprotective amount of the vHBsAg together with a suitable carrier.

Other aspects of the invention are described hereinbelow.

The vHBsAg and vaccine of the invention may be used to overcome the problems perceived by the emergence of an 'escape mutant' as defined hereinabove in which the 'a' determinant of the viral HBsAg has undergone modification. In particular the vaccine of the invention has the advantage that it may be used to protect against, and prevent the emergence or transmission of, a variant HBV which is defined herein as having a modified 'a' determinant in the HBsAg amino acid sequence wherein there is an amino acid other than glycine at position 145.

Accordingly there is also provided a method for protecting a human against disease symptoms associated with infection with said variant HBV, which method comprises administering to the human a safe and effective amount of the vaccine according to the invention.

In another aspect the present invention provides vHBsAg for use in therapy, especially prophylaxis.

The invention also provides the use of vHBsAg in the manufacture of a vaccine composition for protecting a human against disease symptoms associated with said variant HBV infection.

When used to immunise humans against an existing variant HBV virus it will be appreciated that the vHBsAg sequence in the vaccine will normally match, or be antigenically equivalent to, the vHBsAg sequence in the variant HBV virus.

Preferably the amino acid at position 145 in the vHBsAg of the invention is such that it may be derived by a point mutation in the GGA codon coding for glycine at position 145 in normal HBsAg.

In a preferred embodiment of the invention the glycine residue at position 145 of normal HBsAg is replaced by a more hydrophillic amino acid since this results in enhanced antigenicity.

In a particularly preferred embodiment of the invention the modification at position 145 in the 'a' determinant of HBsAg is substitution of glycine by arginine, since, as described hereinbelow, this modification has been shown to arise on an HBV variant isolated clinically.

In order to describe the invention more clearly, reference is made to the following figures, in which.

In a further aspect of the invention there is provided a process for preparing the vHBsAg and the vaccine composition obtained therefrom.

Preferably the vHBsAg is obtained synthetically, either by peptide synthesis or more preferably by recombinant DNA techniques.

Figure 1:
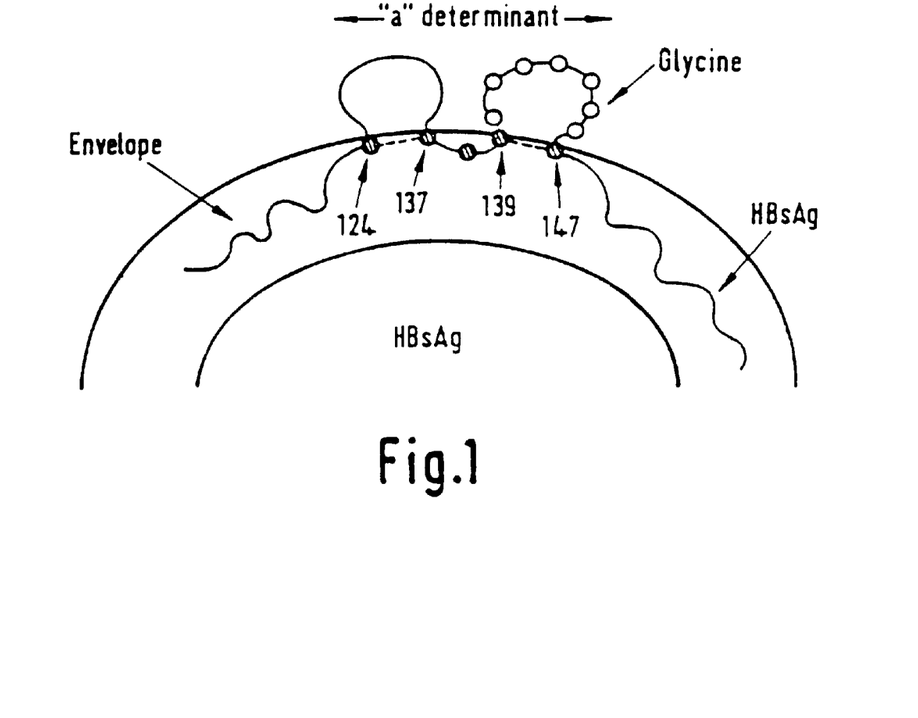
FIG. 1 shows a schematic view of a part of the normal HBsAg amino acid sequence indicating the two loops of the 'a' determinant and the glycine residue at position 145.

Methods for the construction, manipulation and verification of recombinant DNA molecules and sequences are well known in the art. To change glycine into a different amino acid at position 145 of the normal HBV S protein of HBsAg (see FIG. 1) to obtain the vHBsAg of the invention it is required to change the codon GGA at positions 433–435 of the S-gene nucleotide sequence to a different codon encoding the required amino acids.

In a particular embodiment it is preferable to change the GGA codon to, most preferably, AGA or less preferably to CGA or CGC or CGG or CGT or AGG, all of which triplets encode arginine.

Several methods are available to effect the appropriate change of sequence. One suitable method is complete de novc synthesis, by phosphite or phorphoramidite chemistry, of the desired coding sequence using viral or yeast codon frequencies.

Synthesis of DNA is available from several companies on a commercial basis. An example of such gene synthesis is described by Hayden and Mandecki, DNA 7: p571 (1988) and references therein.

A second method is to clone on a single strand vector an appropriate restriction fragment from a vector which already comprises the HBV genome and thereafter effect site specific in vitro mutagenesis as described by Botstein and Shortle, Science, 229, p. 1193 (1982). A culture of E. coli K12 strain C600 containing the recombinant plasmid pRIT10601 comprising an HBV genome of ay subtype cloned on pBR322 was deposited in accordance with the Budapest Treaty in the American Type Culture Collection on Jun. 2, 1982 under Accession Number ATCC 39132. The sequence coding for the S-gene specifying the 226 amino acid HBsAg protein or longer sequences coding for Pre S polypeptides can be excised from such clones by standard recombinant DNA techniques.

One appropriate restriction fragment is the 575 bp XbaI-AccI fragment from within the S-gene coding region of pRIT10601. Vector systems useful for in vitro mutagenesis are commercially available. The mutated gene fragment so obtained is reinserted into the S-gene.

A third method is to effect the desired mutational change using polymerase chain reaction (PCR) technology as described by Ho et al, *Gene*, 77: p51 (1989).

In each case the vHBsAg coding sequence may be expressed under the control of a suitable promoter in any suitable host.

Expression vectors comprising the DNA sequence encoding vHBsAg are novel and form a further aspect of the present invention. Hosts transformed with the said expression vectors form yet another aspect of the invention.

In a preferred aspect *S. cerevisiae*, *Pichia pastoris* or *Hansenula polymorpha* may be used as the host and expression is under the control of a yeast promoter, such as the yeast TDH3 promoter (glyceraldehyde- 3-phosphate dehydrogenase gene, see Valenzuela et al., 1982; Bitter et al., 1988, supra) or PH05 (Miyanohara et al., *Proc. Natl. Acad. Sci. USA* 80, p. 1, 1983), MOX, FMDH (see EP-A-0 299 108) and AOX (see EP-A-0 226 846).

The transformed host can be cultured or fermented by conventional means and the vHBsAg extracted and purified. Purification of HBsAg from yeast cells is well known in the art and can be done according to any of U.S. Pat. Nos. 4,649,192, 4,683,294, 4,694,074 or 4,738,926. Purification of the vHBsAg of the invention is carried out in an analogous manner.

Vaccines containing the vHBsAg are prepared by conventional techniques and will contain an immunoprotective amount of the vHBsAg preferably in buffered physiological saline and admixed or adsorbed with any of the various known adjuvants including aluminium hydroxide and aluminium phosphate. By "immunoprotective" is meant that enough of the vHBsAg is administered to elicit a sufficient protective antibody or cell mediated immune response to confer protection against the infectious agent without serious side effects. The amount of vHBsAg to be administered will depend on whether the vaccine is adjuvated and will generally comprise between 1 to 1000 mcg of protein, for example 1 to 200 mcg protein, more preferably 5 to 40 mcg protein. The amount and number of doses to be administered can be determined in standard dose range studies involving observation of antibody titres and other responses in subjects.

The vHBsAg may also be mixed with other HBsAg such as normal HBsAg or homogeneous or composite HBsAg particles containing all or part or parts of the PreS1 or PreS2 polypeptides for vaccine formulation. It may also be mixed with hybrid HBsAg particles carrying epitopes from proteins from other organisms and with other immunogens to form bivalent or multivalent vaccines. Vaccine preparation is generally described in "Vaccines", edited by Voller et at, University Park Press, Baltimore, Md., U.S.A., 1978.

The vHBsAg is useful for inclusion as an immunological reagent in detection kits for variant HBV virus infection and the like. It can also be used to raise polyclonal and monoclonal antibodies by known methods, some of which monoclonal antibodies may be specific for the variant antigen and not recognise normal HBsAg.

Accordingly in another aspect of the invention there is provided a kit for the diagnostic in vitro detection of anti vHBsAg antibodies in a biological medium, and in particular neutralising antibodies following vaccination, characterised in that it comprises:

a) vHBsAg as herein defined; and b) means adapted to detect the antigen-antibody reaction.

In a further aspect the invention provides an antibody preparation comprising anti-vHBsAg antibodies for use in the prevention or treatment of hepatitis B infection in humans. There is also provided a method of treating humans with an effective amount of such anti-vHBsAg antibody to prevent or treat hepatitis B infection.

The invention will now be illustrated by the following examples.

EXAMPLE 1

Identification of Variant Hepatitis B Virus ('Escape Mutant')

(a) Methods (i) Immunisation with HBV vaccine

A number of trials of HBV vaccine were begun in Italy in 1982. Several centres took part, one of which, the Fourth Division of Infectious Diseases at Hospital D. Cotugno in Naples, followed up 1590 people. The region from which most of these patients came, Campania, has an HBsAg prevalence of greater than 5%. The patients were mostly infants of HBsAg positive carriers, from two regions of southern Italy, who were vaccinated with either HB-VAX (Merck Sharp and Dohme) or HEVAC-B (Pasteur), both plasma-derived vaccines. Doses of 20 ug of the former for adults (10 ug for infants) at 0, 1 and 6 months or 5 $\mu$g of the latter at 0, 1, 2 and 14 months were given. Babies were also given 0.5 ml hepatitis B hyperimmuneglobuliin (HBIg) (Biagini), prepared by the Chon ethanol fractionation procedure, at birth and at 1 month of age. A number of family contacts of carriers, both adults and children, were also vaccinated.

(ii) Hepatitis markers

Blood samples were tested for HBsAg, HBeAg, anti-HBe, anti-HBs and anti-HBc using commercial kits (Abbott Laboratories). Anti-HBs were estimated by comparison with a standard curve generated with a quantitation panel (Abbott Laboratories). HBsAg positivity was confirmed both by retesting and by neutralisation using the HBsAg Confirmatory Assay (Abbott Laboratories). HBsAg neutralisations were performed using a serum containing almost exclusively anti-a. Sera from patients with markers of viral replication were also tested for alanine aminotransferase (ALT) levels.

(iii) HBsAg and anti-HBs subtyping

Subtyping HBsAg was performed on the carrier contacts of 5 infected babies and 5 infected children, 6 of 8 of the family contacts of infected adults and cases AS, AA and AE as well as 2 of the adult cases. For subtyping, beads coated with anti-a, anti-d, or anti-y (Sorin Biomedica) were incubated overnight at room temperature with serum. After washing with distilled water, 13.2 $\mu$Ci $^{125}$I sheep anti-HBs was added, left for 1 hour at 45° C., washed and quantified in a scintillation counter. A sample was considered ay when the counts obtained using either anti-a or anti-y on the solid phase exceeded 2.1 times the negative control mean value (of 7 healthy HBV negative persons) and that obtained with the anti-d beads was lower than the cut-off value. Samples were considered to have only y reactivity if the counts were higher than the cut-off value when added to anti-y on the solid phase, but lower than the cut-off value when added to anti-a or anti-d solid phases.

Specificity of reactivity was confirmed by neutralisation with monoclonal antibodies (Sorin Biomedica). HBsAg positive sera were mixed with monospecific anti-a, anti-d or anti-y antibody before subtyping. A reference HBsAg-containing serum was used as a control.

Anti-HBs subtyping was performed on cases AS, AA and 2 or the adult cases, using a sandwich RIA which employs a recombinant HBsAG (rHBsAg) of one subtype on the solid phase and a radioiodinated one of a different subtype as the probe. Polystyrene beads were coated with either ad or ay rHBsAg. To detect anti-a, 0.2 ml of serum was incubated overnight at room temperature with beads. After washing, the beads were incubated with radioiodinated rHBsAg for 2 hours at 40° C. After washing, the radioactivity of the beads was counted. For the ad subtype assay, beads coated with ad were probed with labelled ad rHBsAg and similarly for the ay assay. Specimens with counts above 4 times the mean of the negative control were positive. Titre were expressed as mIU/ml compared to a standard panel. The percentage of anti-a in a serum was determined by calculating the anti-a over anti-ad or anti-ay times 100.

(iv) Patients for sequencing studies

An HBsAg, HBeAG and anti-HBc positive carrier (patient IE) with an ALT of 105 was delivered of a male infant (AS) on Mar. 5, 1983. The father as anti-HBc and anti-HBs positive. At birth and 1 month later, the infant was given 1.5 ml of HBIg and he was vaccinated with HB-VAX (Merck Sharp and Dohme) at 3 months, 4 months and 9 months of age. For sequencing studies, sera were chosen from the mother at delivery, the child at 11 months of age (HBsAg, HBeAg and anti-HBc positive; anti-HBs 420 mIU/ml; ALT 120) and 5 years later (HBsAg and HBeAg positive, anti-HBs negative; ALT 36). Sera from 4 randomly chosen Italian HBeAg positive carriers not involved in the study, and from 3 British HBsAg positive patients were also sequenced.

(v) PCR and direct sequencing

Figure 2:
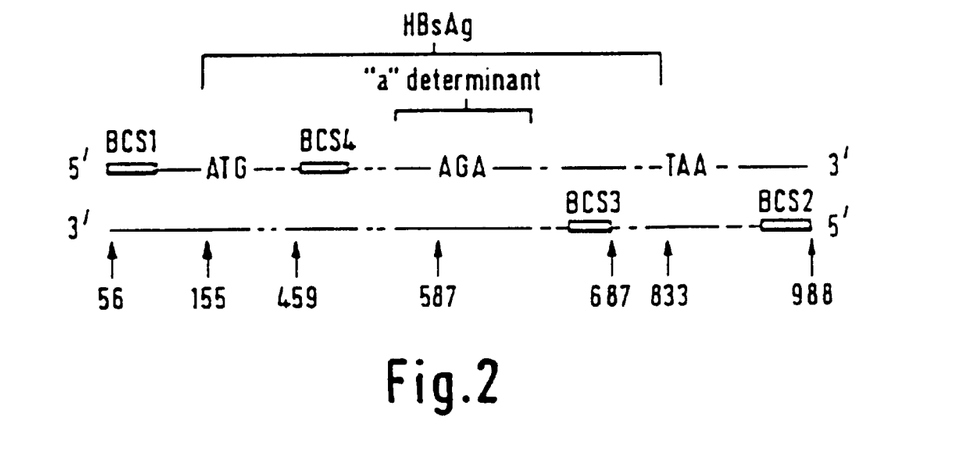
FIG. 2 shows a schematic view of the nucleotide sequence of a clinically isolated variant HBsAg, indicating primer binding sites used for PCR and sequencing and the AGA codon found at positions 587–589 resulting from a G to A point mutation at position 587 in the normal sequence.

50 µl serum was digested in 25 mM sodium acetate, 2.5 mM EDTA, 0.5% SDS and 1 mg/ml proteinase K (Boehringer Mannheim), in a volume of 200 µl overnight at 37° C. After 2 phenol/chloroform and 2 chloroform extractions, the DNA was precipitated with ethanol and the pellet washed with 70% ethanol. The pellet was resuspended in 20 µl of water. PCR was performed on 10 µl of the DNA with 300 pmol each of primers BCS2 and BCS4 using the method of Carman et al, *Lancet*, 1989, ii, 588–591. Details of the target sequence, primer binding sites and primer sequences are given in FIG. 2.

After agarose gel electrophoresis of 10 µl of the reaction to confirm the presence of amplified DNA, the remainder was spun through a G-50 Sephadex column (Pharmacia) and precipitated with ethanol. After 3 washes with 70% ethanol, the pellet was resuspended in 20 µl of water. Meanwhile, 10 pmol of sequencing primer BCS3 was endlabelled in a standard buffer with 10 µCi gamma$^{32}$P-ATP using 10 U polynucleotide kinase (Boehringer Mannheim) in a final volume of 20 µl. The sequencing primer was not column-purified after labelling.

4 µl of the DNA was added to 4 µl of labelled BCS3 in the presence of 2 µl of 5× buffer, as supplied in the Sequenase kit (United States Biochemicals), heated to 95° C. and cooled slowly to 50° C. The manufacturer's recommendations were followed except that the labelling step was omitted and the termination mixes were diluted with an equal volume of water. Reactions were electrophoresed on a 5% Sequagel (National Diagnostics) polyacrylamide-urea gel.

(vi) Hydrophobicity plots

Amino-acids 139 to 147 of the 'a' determinant from the normal and the mutant HBsAg were analysed using Prosis (Pharmacia) software.

(b) Results (i) Subtyping studies

Of the 1590 vaccines, 44 (2.8%) developed HBsAg, of whom 12 showed weak reactivity and no other HBV markers. Details were obtained on 18 of these patients: 5 infants born to carrier mothers, 5 child family contacts and 8 adult family contacts.

The subtype of HBV was determined to be ay in all the contacts of the infected infants and children and in 6 of the 8 (all those tested) of the contacts of adult cases. The mother of case AS was found to be ay on 2 occasions, the first time 2 months after delivery. Patient AS was found to be weakly positive for subtype y at 12 and 18 months of age and ay positive at 46 months, 6 months after the anti-HBs became undetectable. Case AA at 2 years after the beginning of vaccination, case AE 9 months later and both adult cases (26 and 28 months after immunisation) were y positive only.

These results were confirmed using monoclonal reagents. All the cases with y-containing sera were neutralised with anti-y but not anti-a.

Subtyping of anti-HBs revealed that 50–70% of the antibodies were anti-a. In patient AS, at 6 months of age and thereafter, about 90% was against the a determinant.

(ii) Sequencing of the 'a' determinant

Patient AS was found by sequencing to have a single mutation from guanosine to adenosine (G to A) at position 587 (numbered from the unique Eco R1 site of the HBV genome), resulting in an amino-acid substitution from glycine to arginine at amino-acid 145 of HBsAg. This change was shown to be stable, as it was present both at the age of 11 months and at 5 years of age. The mother, IE, and the control patients had glycine at this point in the epitope, as in all sequences published to date. The sequence of the a determinant was otherwise the same in patients AS and IE and the same as those previously published.

(iii) Hydrophobicity plots

The relative hydrophobicity of the second loop of the a determinant of normal HBsAg and that from patient AS was determined. Using the method of Kyte and Doolittle, *J. Mol. Biol.* 1982, 157, 105–132, the mean hydrophobicity index for the second loop was found to have changed from −1.3 to −1.9, and from −0.5 to −0.9 using the method of Hopp and Woods (*Proc. Natl. Acad. Sci. U.S.A.,* 1981, 78, 3824–3828).

EXAMPLE 2

Construction of a variant S-gene coding sequence of av serotype containing a gly to arg replacement at amino acid position 145

Four oligonucleotide primers, BC17, BC144, BC145, and BC146, having the sequences shown below were synthesized by conventional phosphoramidite chemistry on a Biosearch 8600 DNA synthesizer according to the manufacturers instructions.

BC17 5'GTCTAGACTCGTGGTGGACT 3'
BC144 5'TTGGAATTCGTTAAATGTATA3'
BC145 5'CTTCGGAC<u>AGA</u>AATTGCACCT 3'
BC146 5'AGGTGCAATT<u>TCT</u>GTCCGAAG3'

Figure 3:
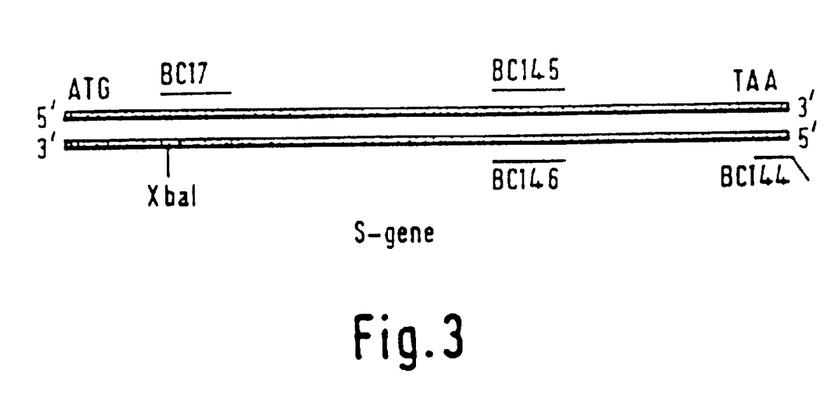
FIG. 3 shows a diagrammatic representation of the S-gene on plasmid pRIT10601 or pRIT 13438 indicating oligonucleotide binding sites for the polymerase chain reaction (PCR)
Figure 4:
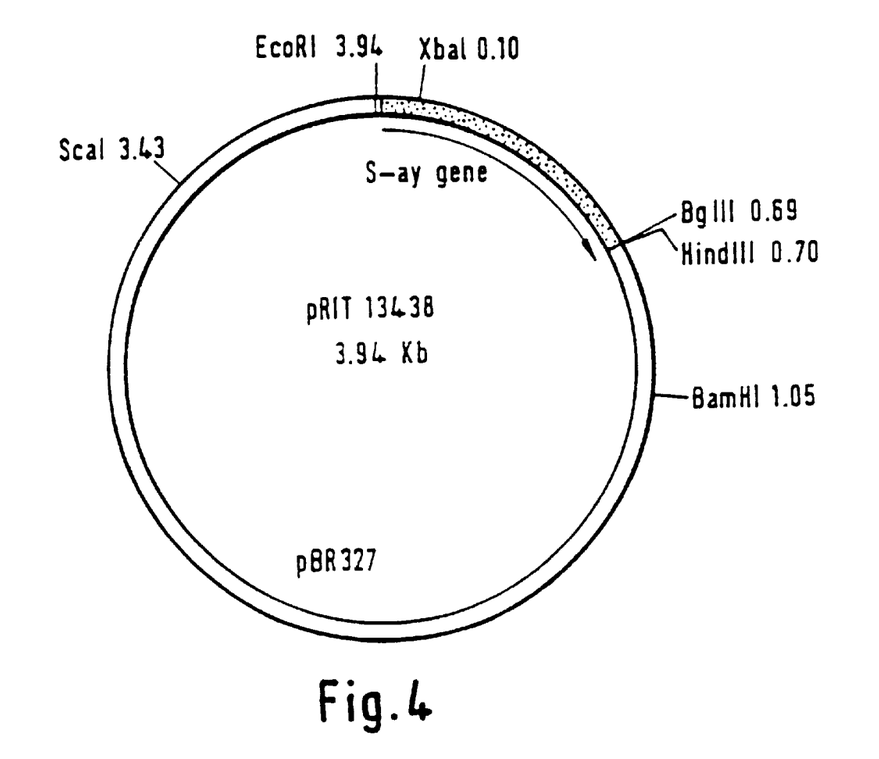
FIG. 4 shows a diagrammatic representation of the plasmic pRIT13438.

These oligonucleotides have homology to the ay S-gene sequence on pRIT10601 as shown in FIG. 3 and are used as primers for nucleotide extension by Tag polymerase with the ay S-gene as template. The underscored AGA and TCT triplets on BC145 and BC146 encode the desired arg145 substitution. Furthermore the sequence GAATTCG on BC144 enables introduction of an EcoRI restriction site one bp distal to the TAA termination codon of the S-gene coding sequence. The PCR reaction is carried out as specified by the manufacturer (Perkin Elmer Cetus) using either pRIT10601 or the plasmid pRIT13438 shown in FIG. 4 as template. pRIT13438 is a conventional *E. coli* vector containing a complete ay S-gene coding sequence derived from pRIT10601 and flanked by EcoR1 and BglII restriction sites introduced by in vitro manipulation. About 1 to 10 ng of template DNA is mixed with 50 mM KCl, 10 mM Tris-HCl pH 8.3, 1.5 mM MgCl$_2$, 0.01% (w/v) gelatin, 200 µM each of dATP, dGTP, dCTP, and dTTP, 1 µM of each desired primer and 2.5 units of Tag polymerase in a final volume of 100 microliters. Two separate reactions are set up, one containing BC17 and BC146 with the template, the other containing BC144 and BC145 with the template.

The two mixtures are subjected to 25 cycles of denaturation (2 min, 94° C.), annealing (2 min, 48° C.) and extension (2 min, 72° C.) followed by one cycle with a 15 minute extension time at 72° C. using a DNA Thermal Cycler (Perkin Elmer Cetus, obtained from Van der Heyden, Brussels, Belgium). The presence of the desired amplified fragment in each mixture is verified by conventional agarose gel electrophoresis and fragments are purified by passage over Centricon 100 columns (Amicon Division, W. R. Grace and Co, obtainable from Van der Heyden, Brusesls, Belgium). About 1 to 10 ng of each amplified fragment is mixed in a single reaction with primers BC17 and BC144 and amplified exactly as described above except that the annealing reaction takes place at 60° C.

Additional oligonucleotide primers BC90 and BC153 having the sequences shown below may also be used in place of BC17 and BC144.

BC90 5'ATGGAGAACATCACATCAGCATTC-CTAGGA 3'

BC153 5'TTGGAATTCGTTAAATGTATACCCAAA-GACAAAA 3'

BC90 has homology to the 5' end of the ay 5-gene sequence starting at the initiation codon. BC153 overlaps BC144.

Two PCR reaction mixtures were set up, containing in one BC90 and BC146 together with pRIT13438 DNA as template and other ingredients as detailed above, and in the other BC145 and BC153 together with pRIT13438 as template and other ingredients as detailed above. The two mixtures were then subjected to 25 cycles of denaturation (2 min., 94° C.) annealing (2 min., 48° C.) and extension (2 min., 72° C.) to permit amplification. The desired 445 bp fragment from the BC90/BC146 amplification and the 267 bp fragment from the BC145/BC153 amplification were purified by polyacrylamide gel electrophoresis and electro-elution.

About 10 ng of each fragment were then mixed and subjected to 25 cycles of PCR amplification in the presence of oligonucleotides BC90 and BC153 in the same reaction conditions as described above. The resulting amplified fragment of about 690 bp was recovered and contains single recognition sites for Xbal and EcoRI endonucleases.

Figure 5:
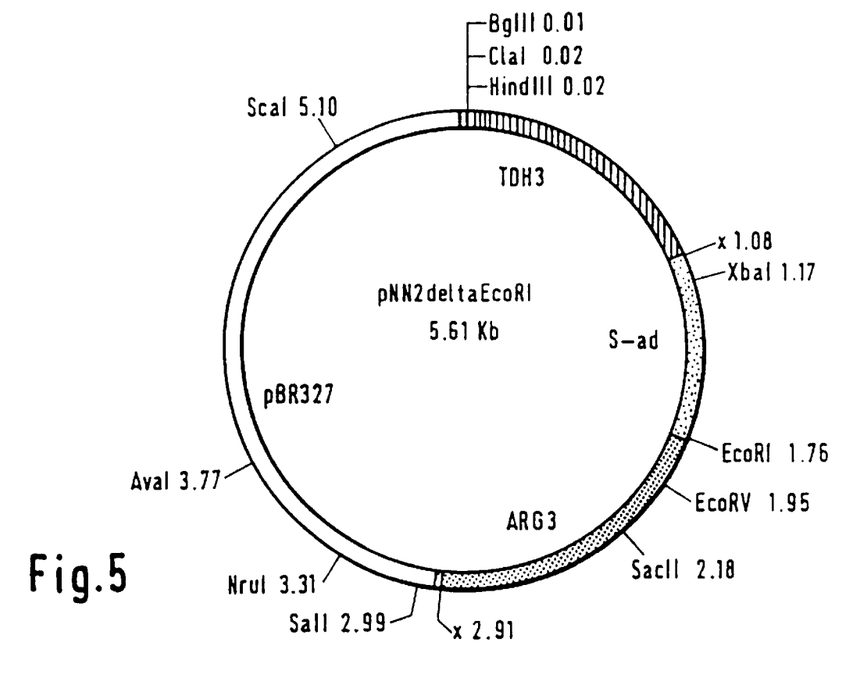
FIG. 5 shows a diagrammatic representation of the plasmic pNN2deltaEco RI.
Figure 6:
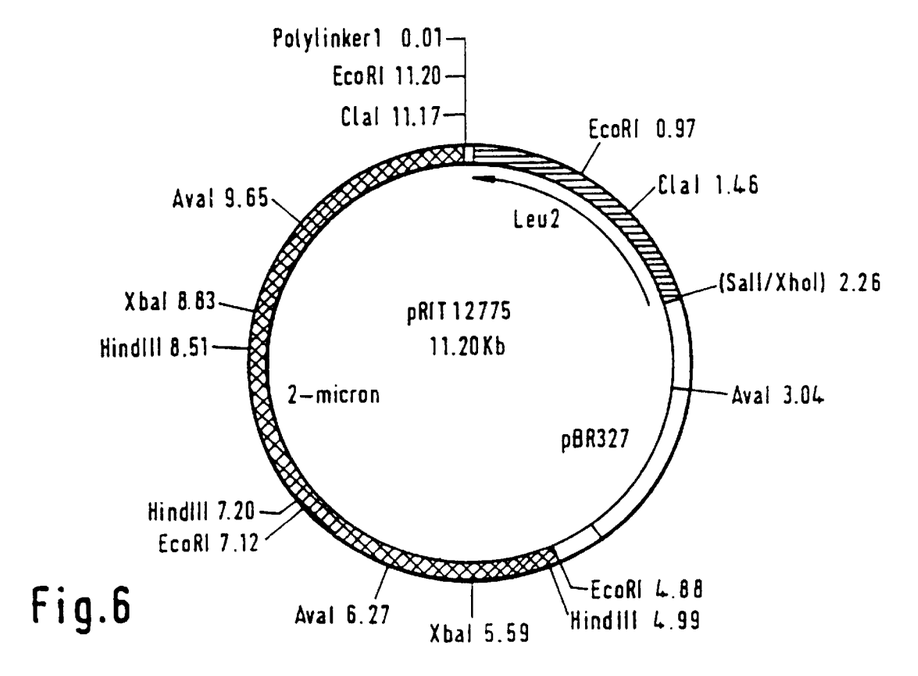
FIG. 6 shows a diagrammatic representation of the plasmic pRIT12775. Polylinker 1 is as follows: 0.01/BglII.ClaI.HindIII.BamHI.AvaI.SmaI.AvaI.XhoI.SalI.

Use of these specific oligonucleotide primers, ay S-gene template and the PCR reaction results in the production of a variant 590 bp S-ay fragment having the arg145 substitution and 5'XbaI, 3' EcoRI extensions. The desired fragment is preferably purified from primers and other products of the PCR reaction by passage over a Centricon 100 column. The fragment is then substituted by conventional cloning techniques for the corresponding XbaI - EcoRI fragment of a normal viral coding sequence preferably fused to a yeast promoter. A vector suitable for this purpose is pNN2deltaEcoRI shown in FIG. 5 where an ad serotype S coding sequence has been fused to the yeast TDH3 promoter and is upstream of the yeast ARG3 transcription terminator to form an expression cassette. The construction and use of such expression cassettes are taught in EP-A-0 278 940. It will be appreciated by one skilled in the art that any suitable vector of this type may be employed depending on the promoter and transcription terminator fragments selected to control expression in the yeast species chosen as host. Furthermore, other restriction sites could be introduced at the 3' end of the variant fragment by using primers other than BC144. It will be appreciated further that all nucleotide differences resulting in amino acid changes between known HBV isolates of adw and ayw serotypes reside downstream of the XbaI site so that substitution on pNN2deltaEcoRI of the variant XbaI - EcoRI fragment obtained by PCR results in an ayw coding sequence.

About 1.5 mcg of the 690 bp fragment resulting from the PCR reactions with BC90, BC153, BC145 and BC146 described above was digested with XbaI and EcoRI endonucleases and about 0.15 mcg of the digested fragment was mixed and ligated with about 50 ng of the vector pRIT12642 which had been digested with Xbal and EcoRI endonucleases and dephosphorylated. pRIT12642 is exactly identical to the pNN2deltaEcoRI vector shown in FIG. 5. From the ligation mixture, a plasmid was recovered and identified as pRIT13555 which contains the Xbal-EcoRI fragment carrying the modified S-coding sequence inserted between the Xbal and EcoRI sites of the pRIT12642 vector, so as to form an expression cassette where the variant ay coding sequence is situated 3' to, and under the control of, the TDH3 promoter.

The resulting vHBsAg expression cassette obtained as described above is excised from the pNN2deltaEcoRI derivative plasmid as a 2.89 kb fragment by digestion with BglII and SalI endonucleases and inserted on any vector of choice for introduction in yeast. A suitable multicopy vector for *S. cerevisiae* is pRIT12775 shown diagrammatically in FIG. 6 which contains a polylinker inserted between the EcoRI and SalI sites on the pBR327 replicon and which was constructed by conventional DNA manipulation techniques using well known DNA fragments. The 2.98 BglII-SalI cassette fragment from pRIT13555 was obtained by endonuclease digestion and inserted between the BglII and SalI sites of pRIT12775 by conventional cloning techniques to form the plasmid pRIT13557. If it is desirable to integrate the cassette into the yeast genome an integrative vector such as those described in Jacobs et al, *Gene,* 80, page 279 (1989), is preferred. When proceeding with the insertion of the vHBsAg expression cassette on pRIT 12775, yeast cells of a leucine2 deficient mutant are transformed by the method of Ito et al, *J. Bacteriol.* 153: p163 (1983) with selection for leucine independent transformants. A suitable recipient strain with a double leu2 mutation is strain DC5 deposited under the Budapest Treaty with the American Type Culture Collection on Jun. 2, 1982 under accession number ATCC 20630.

A further suitable strain is a cir$^o$ derivative of DC5 which was deposited under the Budapest Treaty with the American Type Culture Collection on Aug. 18, 1986 under accession number ATCC20820. Strain DC5 cir$^o$ was transformed with DNA of pRIT13557 by the method of Ito et al cited above with selection of leucine independent colonies. A transformant colony was retained and subcultured to establish the strain identified as Y1648.

An expression cassette carrying the vHBsAg coding sequence may also be transformed into host cells of *S. cerevisiae, H. polymorpha* or *P. pastoris* which carry other expression cassettes so as to form composite HBsAg particles which contain a mixture of two or more polypeptide species.

Conventional cloning techniques were used to construct a 2.98 kb expression cassette consisting of the yeast TDH3 promoter, the coding sequence of the S-gene of ay subtype from pRIT10601 and the yeast ARG3 terminator fragment. This cassette was then inserted between the BglII and SalI sites of pRIT12775 to form pRIT13558. pRIT13558 was then introduced by transformation, using the technique of Ito et al cited above, into the recipient strain DC5 cir$^o$ with selection for leucine independence. A transformant colony was retained and subcultured to establish the strain identified as Y1654.

Strain Y1654 expresses HBsAg of ay subtype which is useful as a control when investigating the properties of the vHBsAg of the present invention, Subcloning and expression of ay subtype particles in yeast using pRIT10601 as starting material and the yeast ARG3 promoter has been described by De Wilde et al in Devel. Biol. Standard. 59, 99–107 (1985).

Cultures of Y1648 and Y1654 were grown and the HBsAg extracted and measured in the crude cell extracts by AUSRIA radioimmunoassay (Abbott Laboratories, North Chicago, Ill., U.S.A.). The results of assaying two cultures of each of Y1648 and Y1654 are shown below.

| STRAIN | CULTURE NUMBER | PROTEIN (g/l culture) | HBsAg by AUSRIA (g/l culture) | HBsAg as percent protein |
|---|---|---|---|---|
| Y1648 | C1316 | 23.42 | 0.0115 | 0.049 |
|  | C1324 | 27.30 | 0.0131 | 0.05 |
| Y1654 | C1332 | 20.12 | 0.127 | 0.63 |
|  | C1336 | 26.09 | 0.136 | 0.52 |

Strain Y1648 produces about 10-fold less apparent AUSRIA reactive material compared to strain Y1654. Western blotting of crude cell extracts using monoclonal antibody HBS1 (SmithKline Beecham Biologicals, Rixensart, Belgium), recognizing the denatured and reduced HBV surface antigen polypeptide, showed that Y1648 produced about the same amount of HBS1 reactive protein with a molecular weight of 24K as did Y1654.

Methods for the culture of yeast cells, extraction and assay of HBsAg and Western blotting may be found in EP-A-0 278 940 and EP-A-0 414 374 both of which are incorporated herein by reference.

Surface antigen material was purified from cell extracts of both Y1648 and Y1654 by conventional methods according to U.S. Pat. Nos. 4,649,192 and 4,683,294 cited above.

The preparations consisted of substantially pure HBV surface antigen protein as analyzed by SDS-PAGE and silver staining which revealed single major bands of protein at 24K together with traces of dimers and multimers.

Two preparations of yeast derived HBsAg from strain Y1654 gave AUSRIA/protein ratios of 1.64 and 2.79 whereas two vHBsAg preparations from strain Y1648 gave diminished AUSRIA/protein ratios of 0.1 and 0.13.

Purified vHBsAg from strain Y1648 was examined by electron microscopy after staining with uranyl acetate. The material showed the presence of spherical particles typical for HBV surface antigen.

EXAMPLE 3

Preparation of a Vaccine Composition

To a sterile, buffered aqueous solution of 3% aluminium hydroxide in 10 mM sodium phosphate, 150 mM NaCl, pH6.8, the vHBsAg of Example 2 in similar buffer is added with constant stirring to a final concentration of 5 to 40 mcg protein and 0.5 mg per ml of aluminum ($Al^{3+}$). Thimerosal (sodium merthiolate) is then added to a 1 in 20,000 (w/v) final concentration as preservative.

The vaccine is suitable for parenteral administration to humans.

What is claimed is:

1. An isolated antibody preparation comprising antibodies raised against or which detect a variant hepatitis BS (vHBsAg) protein or fragment thereof, said vHBsAg protein or fragment thereof comprising a modified 'a' determinant of an S(HBs) protein in which the amino acid at position 145 of the HBs protein is arginine, said vHBsAg displaying an antigenicity different from that of wild-type S (HBsAg) protein.

2. An isolated antibody preparation as claimed in claim 1, wherein the protein is identical to wild-type HBsAg except for the altered amino acid residue at position 145.

3. An isolated antibody preparation comprising antibodies raised against or which detect a variant hepatitis BS (vHBsAg) protein or fragment thereof, said vHBsAg protein or fragment thereof comprising a modified 'a' determinant of an S(HBs) protein in which the amino acid at position 145 can be derived by point mutation in the GGA coding coding for glycine at position 145 in wild-type HBsAg so that the point mutation codon at position 145 then codes for arginine, said point mutation codon being selected from the group consisting of AGA, CGA, CGC, CGG, CGT, and AGG.

4. An isolated antibody preparation as claimed in claim 1, wherein the protein comprises a sequence of a vHBsAg in which there are point mutations or insertions giving rise to at least one altered or additional amino acid residue at a position other than position 145 of the wild-type HBsAg sequence.

5. An isolated antibody preparation as claimed in claim 1, wherein the vHBsAg includes a pre S coding sequence.

6. An isolated antibody preparation as claimed in claim 5, wherein the pre S coding sequence is a Pre S1 coding sequence.

7. An isolated antibody preparation as claimed in claim 5, wherein the pre S coding sequence is a Pre S2 coding sequence.

8. An isolated antibody preparation as claimed in claim 4, wherein the vHBsAg includes a Pre S coding sequence.

9. An isolated antibody preparation as claimed in claim 8, wherein the Pre S coding sequence is a Pre S1 coding sequence.

10. An isolated antibody preparation as claimed in claim 8, wherein the Pre S coding sequence is a Pre S2 coding sequence.

* * * * *

UNITED STATES PATENT AND TRADEMARK OFFICE
CERTIFICATE OF CORRECTION

PATENT NO.    : 6,099,840
DATED         : August 8, 2000
INVENTOR(S)   : Thomas et al.

It is certified that error appears in the above-identified patent and that said Letters Patent is hereby corrected as shown below:

<u>Title page,</u>
Under "Foreign Application Priority Data" delete "Apr. 29, 1990" and replace by -- Mar. 29, 1990 --.

Signed and Sealed this

Seventh Day of May, 2002

*Attest:*

JAMES E. ROGAN
*Attesting Officer*     *Director of the United States Patent and Trademark Office*